United States Patent
Goldring et al.

(10) Patent No.: US 8,195,011 B2
(45) Date of Patent: Jun. 5, 2012

(54) ELECTRO-OPTICAL MODULATOR STRUCTURE

(75) Inventors: Damian Goldring, Ramat Gan (IL); David Mendlovic, Tel Aviv (IL)

(73) Assignee: Ramot At Tel-Aviv University Ltd., Tel Aviv (IL)

( * ) Notice: Subject to any disclaimer, the term of this patent is extended or adjusted under 35 U.S.C. 154(b) by 455 days.

(21) Appl. No.: 12/396,550

(22) Filed: Mar. 3, 2009

(65) Prior Publication Data

US 2009/0220184 A1 Sep. 3, 2009

Related U.S. Application Data

(60) Provisional application No. 61/033,177, filed on Mar. 3, 2008, provisional application No. 61/040,987, filed on Mar. 31, 2008.

(51) Int. Cl.
| | |
|---|---|
| *G02F 1/01* | (2006.01) |
| *G02F 1/035* | (2006.01) |
| *G02B 26/00* | (2006.01) |
| *G02B 1/00* | (2006.01) |
| *G02F 1/03* | (2006.01) |
| *G02F 1/07* | (2006.01) |

(52) U.S. Cl. .......... 385/2; 385/1; 359/237; 359/245; 359/254

(58) Field of Classification Search .......... 385/1, 2
See application file for complete search history.

(56) References Cited

U.S. PATENT DOCUMENTS

| | | | |
|---|---|---|---|
| 7,099,549 B2 * | 8/2006 | Scheuer et al. | 385/132 |
| 7,184,629 B2 * | 2/2007 | Montgomery et al. | 385/39 |
| 7,415,178 B2 * | 8/2008 | Montgomery et al. | 385/39 |
| 2006/0215949 A1* | 9/2006 | Lipson et al. | 385/2 |
| 2009/0190875 A1* | 7/2009 | Bratkovski et al. | 385/2 |

OTHER PUBLICATIONS

Barrios, C. A. et al., "Electrooptic modulation of silicon-on-insulator submicrometer-size waveguide devices", J. of Lightwave Tech., vol. 21, No. 10, pp. 2332-2339 (Oct. 2003).

Barrios, C. A. et al., "Modeling and analysis of high speed electro-optic modulator in high confinement silicon waveguides using metal-oxide-semiconductor configuration", J. of App. Phys., vol. 96, No. 11, pp. 6008-6015 (Dec. 2004).

Coppola, G. et al., "Simulation and analysis of high-efficiency silicon optoelectronic modulator based on a Bragg mirror," Opt. Eng., vol. 40, No. 6, pp. 1076-1081 (Jun. 2001).

Cutolo, A. et al., "An electrically controlled Bragg reflector integrated in a rib silicon on insulator waveguide," App. Phys. Lett., vol. 71, No. 2, pp. 199-201 (Jul. 1997).

(Continued)

*Primary Examiner* — Rhonda Peace
(74) *Attorney, Agent, or Firm* — Houston Eliseeva, LLP

(57) ABSTRACT

The present invention discloses an ultra-compact optical modulator comprising at least one resonator on a semiconductor chip. The EO modulator modulates incoming light having a certain wavelength range and comprises a waveguide layer accommodating at least one resonator having a periodic complex refraction index distribution structure defining a periodic defect band-edge and a cladding layer; and at least one electrode; the waveguide layer, the cladding layer and the electrode forming a capacitor structure; such that when an external voltage is applied to the capacitor structure the free carrier concentration in the waveguide layer is controlled, enabling a modulation of the resonator's refractive index; wherein the periodic defect band-edge is selected to be within the wavelength range, enabling a slow-light propagation of the incoming light within the waveguide layer.

46 Claims, 11 Drawing Sheets

OTHER PUBLICATIONS

Dainesi, P. et al. "CMOS compatible fully integrated Mach-Zehnder interferometer in SOI technology," IEEE Photonics Technology Letters, vol. 12, No. 6, pp. 660-662 (Jun. 2000).

Goldring, D. et al., "Highly dispersive micro-ring resonator based on one dimensional photonic crystal waveguide—Design and analysis," Optics Express, vol. 15, No. 6, pp. 3156-3168 (Jan. 2007).

Liu, A et al., "A high speed silicon optical modulator based on metal-oxide semiconductor capacitor," Nature, vol. 427, pp. 615-618 (Feb. 2004).

Mueller, G. et al., "Optical resonator with steep internal dispersion," Phys. Rev. A, vol. 56, No. 3, pp. 2385-2389 (Sep. 1997).

Soljacic, M. et al., "Enhancement of microcavity lifetimes using highly dispersive materials," Phys. Review E., vol. 71, 026602 (2005).

Soref, R. A. et al., "Electro-optical effects in silicon," IEEE J. of Q. Elec., vol. QE-23, No. 1, pp. 123-129 (Jan. 1987).

Stepanov, S. et al., "Modulation of light by light in silicon-on-insulator waveguides," App. Phy. Lett., vol. 83, No. 25, pp. 5151-5153 (Dec. 2003).

* cited by examiner

ELECTRO-OPTICAL MODULATOR STRUCTURE

RELATED APPLICATIONS

This application claims the benefit under 35 USC 119(e) of U.S. Provisional Application Nos. 61/033,177 filed on Mar. 3, 2008, and 61/040,987 filed on Mar. 31, 2008, both of which are incorporated herein by reference in their entirety.

FIELD OF THE INVENTION

The present invention relates generally to an electro-optical modulator structure and to different applications using the electro-optical modulator.

BACKGROUND OF THE INVENTION

The following references are considered to be pertinent for the purpose of understanding the background of the present invention:

[1] G. Muller, M. Muller, A. Wicht, R. H. Rinkleff, and K. Danzmann, "Optical resonator with steep internal dispersion," Phys. Rev. A 56, 2385-2389 (1997).
[2] M. Soljacic, E. Lidorikis, L. Vestergaard Hau, J. D. Joannopoulus, "Enhancement of microcavities lifetime using highly dispersive materials," Phys. Review E. 71, 026602 (2005).
[3] Damian Goldring, Uriel Levy and David Mendlovic, "Highly dispersive micro-ring resonator based on one dimensional photonic crystal waveguide—Design and analysis"—Optics Express, 15, 3156-3168 (2007)
[4] R. A. Soref, B. R. Bennet, "electro-optical effects in silicon", IEEE J. of Q. Elec. QE-23, 123-129 (1987)
[5] A Liu, R. Jones, L. Liao, D. Samara-Rubio, D. Rubin, O. Cohen, R. Nicolaescu, M. Paniccia, "A high speed silicon optical modulator based on metal-oxide semiconductor capacitor", Nature 427, 615-618
[6] S. Stepanov, S. Ruschin, "Modulation of light by light in silicon-on-insulator waveguides" App. Phy. Lett. 83, 5151-5153 (2003).

An electro-optical (EO) modulator is an essential component in any optical communication system. An EO modulator is an optical device in which a signal-controlled element is used to modulate light using the electro-optic effect. The phase, the frequency, the amplitude, or the direction of the input light may be affected (modulated). The main features usually required for the EO modulator are high speed, sufficient modulation depth, low losses and, as with any other device, robustness and reliability. The EO modulator may be used for intra-chip communication, in which high speed, small volume, and CMOS process compatibility are required.

Traditional modulators are based on free space optics technology using, for example, polarization rotation. As technology advanced, different types of integrated EO modulators were demonstrated. Most of the modulators are based on either a Mach-Zehnder Interferometer (MZI) configuration, or on a resonant configuration (Fabry-Perot, Ring, etc). In both cases, an electrical signal is used to modulate the free carriers' concentration in the semiconductor to obtain optical modulation. Usually, a semiconductor EO modulator changes the resonant property of a resonator corresponding to an operating wavelength by controlling free carriers of a semiconductor, so as to serve as an optical switch and accordingly to enable rapid transmission of digital signals.

Optical resonators are devices having internal optical path lengths that are much longer than their physical dimensions. Long optical path lengths are produced by multiple reflections of optical rays on mirror surfaces.

Two fundamental types of optical resonators are the Fabry-Perot cavity and the ring resonator. The Fabry-Perot cavity comprises two spaced-apart parallel reflective planes. Resonance (constructive interference of the reflected light) occurs for specific wavelengths of light reflected between the reflective planes, when a wave traveling in the resonator undergoes a $2\pi N$ phase retardation, where N is a whole number. Thus, the transmission resonances are periodic across the spectrum (assuming non-dispersive medium). Instead of reflective planes, reflective gratings can also be used to achieve similar results.

Ring resonators establish resonances in a similar manner, but the distance between the reflective planes is defined by the circumference of a circular waveguide rather than the separation between two reflective planes. The potential applications for such resonators include filters, sensors, optical delay lines, and more.

An important characteristic of optical resonators is its Quality factor (Q-factor) that is inversely proportional to the photon lifetime in the resonator (in time domain). Different applications require different Q-factor values; however, obtaining higher Q-factors for a resonator is typically of high interest. The overall Q factor of a resonator is given by 1/Q=1/Qabs+1/Qrad+1/Qc where Qabs, Qrad, and Qc are the absorption, radiation and coupling quality factors, respectively. Each of the Q-factor terms can be effectively increased by using a highly dispersive material inside the resonator [1, 2].

As for the materials used for the fabrication of the EO modulators, high-index materials (n≈3.5), such as silicon, enable strong light confinement and the fabrication of dense optical circuits. The horizontal confinement of the light is generally obtained by different patterns that are introduced to the substrate, while the vertical confinement is usually created by a low-index or highly reflective layer. For example, for Silicon-On-Insulator (SOI)-based devices, having generally a silicon substrate (Si) layer, and a top cladding (SiO2) layer, the horizontal confinement is created by the difference between the index of refraction of the air and of the SiO2 (n≈1.5).

The optical properties of the silicon are expressed via its complex refractive index. In order to tune the optical characteristics of a SOI-based device, the silicon's refractive index has to be changed, by using, for example, the electrically induced method.

The method for electrically inducing refractive index changes in silicon is based on the modulation of the free carriers' concentration. Free carriers are generally electrically injected to a silicon substrate using a PN junction or a MOS capacitor. The injected carriers produce a change in the silicon's refractive index due to three major effects: (i) free-carrier absorption, (ii) Burstein-Moss effect, and (iii) Coulombic interaction with impurities.

An analytic approximation to refractive index change (according to the Drude Model) is given by [4]:

$$\Delta n_{FC} = -\frac{e^2 \lambda^2}{8\pi^2 c^2 \varepsilon_0 n} \left( \frac{\Delta N_e}{m_{ce}^*} + \frac{\Delta N_h}{m_{ch}^*} \right) \quad (1)$$

where $\Delta N_e$, $\Delta N_h$ are the changes in the free electrons and holes concentrations respectively, and $M_{ce}^*$, $M_{he}^*$ are the effective masses of free electrons and holes respectively. The analytic approximation indicates the phenomenological behavior of the silicon, however, for more accurate calculations, the empirical equation (2) experimentally derived in reference [5] for 1.55 μm wavelength is used:

$$\Delta n_{FC} = -8.8 \times 10^{-22} \Delta N_e - 8.5 \times 10^{-18} (\Delta N_h)^{0.8} \quad (2)$$

The electrons and holes densities are in $cm^{-3}$ units.

Performing analytical calculation of the concentration of free carriers that are injected to a SOI-based device is rather difficult. Basically, the continuity equation is solved for the charge carriers, and the generation rate in case of illumination is calculated [6]. The major obstacle in such a process is the surface recombination which has a strong influence on the charges distribution. Since surface conditions vary from one device to the other, and depend greatly on fabrication processes, it is very difficult to predict the charges distribution. In order to get some approximate results, one may use previously obtained results or perform some preliminary experiments.

SUMMARY OF THE INVENTION

There is a need in the art to improve the performance of electro-optical (EO) modulators, by reducing their size, reducing fabrication costs, increasing modulation depth and speed, and reducing supply power. The present invention combines all of these requirements by providing an ultra-compact optical modulator comprising at least one resonator on a semiconductor chip. The modulator sizes are approximately 5 μm×2 μm. The optical modulator modulates the light by either passing through or reflecting the un-modulated light. The incoming light passes through the optical modulator to the output port only if its frequency matches the resonance frequency of the resonator. By modulating the resonator's resonance frequency, light modulation is produced.

Therefore, there is provided an EO modulator for modulating incoming light having a certain wavelength range comprising: a waveguide layer accommodating at least one resonator having a periodic complex refraction index distribution structure defining a periodic defect band-edge and a cladding layer; and at least one electrode; the waveguide layer, the cladding layer and the electrode forming a capacitor structure; such that when an external voltage is applied to the capacitor structure the free carrier concentration in the waveguide layer is controlled, enabling a modulation of the resonator's refractive index; wherein the periodic defect band-edge is selected to be within the wavelength range, enabling a slow-light propagation of the incoming light within the waveguide layer.

According to another broad aspect of the present invention, there is also provided an optical device comprising at least one resonator having a periodic complex refraction index distribution structure formed by a periodic pattern of defects incorporated inside the resonator and defining a periodic defect band-edge. The resonator is configured for operating with an optical signal having a wavelength range including the periodic defect band-edge, enabling a slow-light propagation of the optical signal within the device, resulting in the modal dispersion increasing within the device, the narrowing of the spectral linewidth of the resonator, and the enhancement of the quality factor of the resonator.

The resonator may be configured as a closed-loop resonator or as a micro-ring resonator. The radius of the resonator may be adjusted to satisfy resonance conditions.

In some embodiments, the periodic complex refraction index distribution structure is configured as a 1D photonic crystal. The resonator may be optically coupled to at least one input/output waveguide. At least a portion of the input/output waveguide may have a periodic complex refraction index distribution structure. The portion of the input/output waveguide may be located outside the coupling region between the input/output waveguide and the resonator.

In some embodiments, the modal dispersion increasing within the resonator enables a reduction in the Free Spectral Range (FSR) of the resonator; the resonator generates ultra sharp peaks yielding ultra-high sensitivity.

The period of the complex refraction index distribution structure is adjusted such that the distribution structure band-gap matches the operation wavelength of the optical signal.

The resonator may be made in a silicon substrate. In particular, the resonator, as well as the whole circuit may be fabricated inside a top layer of a Silicon-On-Insulator (SOI) wafer. The substrate may be any other semiconductor substrate, providing a horizontal confinement of the light. On top of the silicon layer, a silicon-oxide buffer layer operating as an insulator is deposited and then covered by a conducting or semi-conducting electrode. The silicon layer in which the resonator exists, the silicon-oxide buffer layer and the electrode yield a type of MOS capacitor.

By applying a voltage difference between the capacitor's contacts, the free carriers' concentration in the silicon can be modulated, modulating the resonator's refractive index. If the Quality factor of the resonator (i.e. the ratio of resonance frequency and bandwidth) is sufficiently large, even a relatively small modulation of the refractive index would yield a sufficiently large modulation of the resonator's resonance frequency. Thus, the electrical signal applied at the capacitors' contacts is converted to optical modulation of the incoming light.

In another broad aspect of the present invention, a hybrid resonator structure is realized by incorporating a series of periodic defects (i.e. a periodic complex refraction index distribution structure) into a standard resonator (e.g. Micro-Ring Resonators—MRRs).

The addition of these periodic defects enables to control the dispersion within the resonator structure. When the wavelength range of operation approaches the band-edge of the periodic structure, the modal dispersion is significantly increased. The increasing of the dispersion leads to narrowing the spectral linewidth of the resonator. The periodic defects generate a slow light phenomenon in which the propagation of the optical signal within the resonator is done at a very low group velocity (i.e. the velocity is at least tens of times slower than the speed of light in a vacuum). The slow light phenomenon occurs around the band-edge corresponding to the periodic structure, increasing the Q-factor of the resonator and reducing its Free Spectral Range (FSR). The band-edge of the periodic structure is the region where no electromagnetic wave can exist, regardless of the wave vector.

It should be noted that conventional optical elements utilizing the properties of periodic defects pattern (e.g. photonic crystals) are manufactured on photonic crystal substrate (e.g. a two dimensional crystal structure). The resonator of the present invention is a resonator incorporating a periodic defect pattern. This enables a simpler production process, and more degrees of freedom in the adjustment of the periodic band-gap to the wavelength of the operation (i.e. less dependency on the wavelength of operation).

In some embodiments, the resonator of the present invention is configured and operable as a sensor. The sensor may be wavelength selective. The sensor may be configured to identify chemical or biological or any other material in a solid, gas or liquid phase near the sensor. An optical signal is directed toward a resonator or a set of resonators and then directed outside the modulator. A flow line enclosing, for example, biological material or a gas may be located in the area surrounding the resonator of the present invention. The resonator environmental change induces a variation in the refractive index within the resonator. Since the resonance frequency is significantly affected by the sensor environment, the structure of the present invention provides a multipurpose sensor using spectral analysis (i.e. filtering). Such a sensor can be used for bio-chemical applications, temperature/pressure measurements, blood analysis, measuring amounts of different gases in the air etc.

The sensor may be configured and operable to sense laser conditions, for example to sense temperature conditions affecting the laser operation.

Alternatively, by using a tunable laser, or a laser tuned to the resonance frequencies of the resonators, one can verify whether the resonators are on resonance or off resonance.

In some embodiments, the resonator produces a spectral response enabling both low and high sensitivity wavelength selection resulting in a wide dynamic range wavelength selection.

In some embodiments, the resonator produces a unique field distribution at the resonance wavelengths. In addition to the sensing of the existence of a material located in the area surrounding the sensor, the field distribution enables the sensing of the spatial locations of such material. Therefore, the sensor is configured and operable to identify spatial distributions of materials in the area surrounding the sensor. The sensor may also be configured as an optical gyroscope.

There is also provided by the present invention, an EO modulator for modulating incoming light having a certain wavelength range comprising: a waveguide layer accommodating a resonator with embedded periodic defects i.e. having a periodic complex refraction index distribution structure defining a periodic defect band-edge and a cladding layer; and at least one electrode; the waveguide layer, the cladding layer and the electrode forming a capacitor structure; such that when an external voltage is applied to the capacitor structure, the free carrier concentration in the waveguide layer is controlled, enabling a modulation of the resonator's refractive index; wherein the electrode is located on the cladding layer above the waveguide layer in a diagonal direction respectively to the waveguide layer such that the electrical field generated by the electrode and the optical mode of the light within the waveguide layer are not overlapping, substantially reducing optical losses in the modulator.

In some embodiments, the electrode being located on the cladding layer above the waveguide layer is configured and operable to enhance the quality factor of the modulator.

An electrical field is applied to the optical waveguide layer between a pair of electrodes. The pair of electrodes may form a symmetrical structure. One electrode may be a gate electrode, the other electrode being a ground electrode located in a spaced-apart relationship with the resonator, providing a spacer between the ground electrode and the optical field propagating in the waveguide layer.

In some embodiments, the modulator is optically connected to the output of an optical coupler having one input port in which the light is transmitted, and a second input port in which a ground electrode is located.

In the present invention, the electrodes made of conductors or semi-conductor materials are specially designed (topographically) to prevent significant losses in the area of the resonator, avoiding high insertion losses which might lead to very low modulation depth. The electrodes may be non-transparent electrodes, for example made of poly-Si, metals etc., and may also be transparent electrodes made of several materials such as ZnO:Al, $In_2O_3$, IR-ITO and Carbon-Nanotubes (CNTs) sheets.

The modulator may be based on a Fabry-Perot configuration with two reflecting surfaces. The reflecting surfaces may be configured as 1D photonic crystal reflectors.

In some embodiments, the modulator comprises at least one other coupling waveguide optically coupled to the waveguide layer, enabling the coupling of the incoming light from the coupling waveguide to the modulator. The waveguide layer may have a straight configuration. The coupling waveguide may have a curved folded strip configuration facilitating the coupling of the incoming light.

In some embodiments, the modulator is configured and operable as an add-drop filter.

The waveguide layer may comprise a PN junction configured to modulate the refractive index in the waveguide layer upon application of external voltage.

In some embodiments, the waveguide layer comprises a periodic pattern of defects forming at least one of the following: a 1D photonic crystal or a 2D photonic crystal.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

BRIEF DESCRIPTION OF THE DRAWINGS

In order to understand the invention and to see how it may be implemented in practice, embodiments will now be described by way of non-limiting example only, with reference to the accompanying drawings, in which:

FIG. 2b graphically illustrates the dispersion curve of the periodic structure of FIG. 2a;

FIG. 7b schematically illustrates a section scheme beneath the gate electrode of the modulator of FIG. 1a;

DETAILED DESCRIPTION OF THE PREFERRED EMBODIMENTS

Figure 1A:
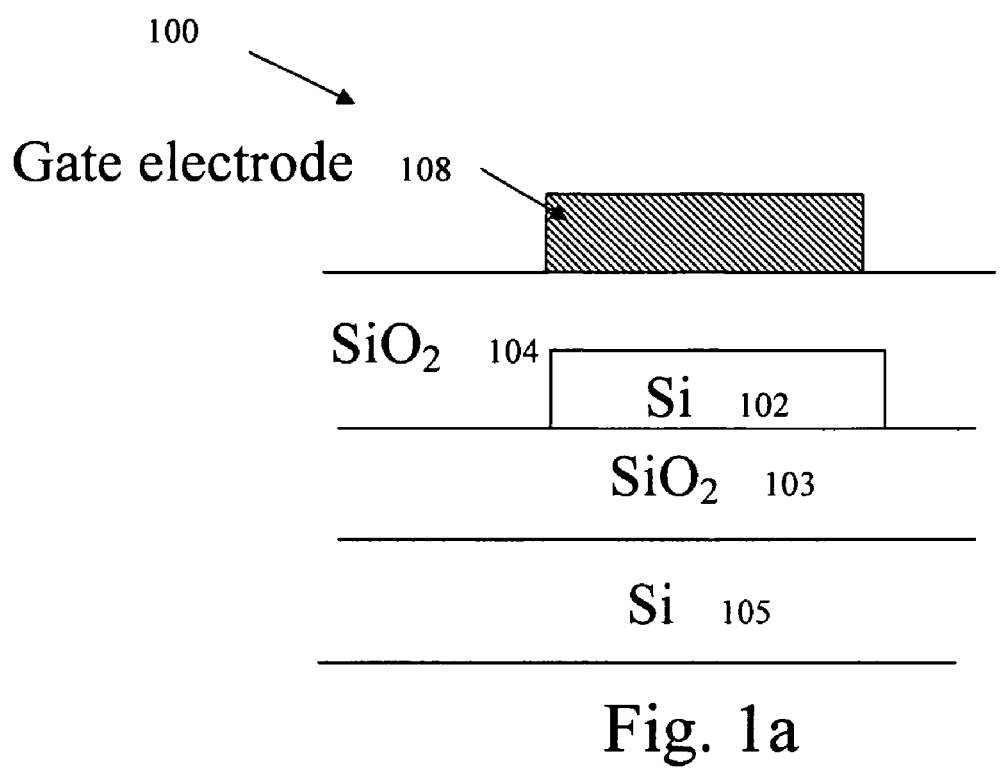
FIG. 1a schematically illustrates a cross-section view of the layer structure forming the electro-optical modulator of the present invention.

The present invention provides a novel high performance EO modulator for modulating incoming light having a certain wavelength range i.e. a wavelength of operation. Reference is made to FIG. 1a, generally illustrating a cross-sectional view of the layer structure forming the modulator of the present invention. To facilitate understanding, the same reference numbers are used for identifying components that are common in all the examples.

In this non-limiting example, the EO modulator structure 100 can be fabricated on a SOI wafer with the following characteristics: 230 nm thick resonator (c-Si) layer 102, 3 µm thick buffer (SiO2) layer 103 and a ~500 µm thick handle (c-Si) layer 105. The top silicon layer 102 deposited on the SiO2 103 is recovered by another SiO2 buffer layer 104, which constitutes the cladding of a ridge waveguide (450 nm wide) that guides light in and out of the SOI chip. The resonator is located on the modulator layer inside the ridge waveguide. On top of the resonator, a gate electrode 108 separated from the silicon layer 102 by an oxide buffer 104 is implemented.

The present invention provides a novel EO modulator having a waveguide layer accommodating a resonator with embedded periodic defects. If a periodic defect, such as a photonic crystal (PhC), is inserted into a resonator, the period may be configured so that the band-edge created by the periodic defect is located at the wavelength of operation. The frequency response of a standard ring resonator is approximately periodic and is composed of transmission peaks or dips (depending on the configuration). However, as explained in reference [3], the frequency response of the resonator with embedded periodic defects comprises a band-gap where no peaks occur, then after crossing the band-edge, peaks appear. The spacing between the peaks determines the Free Spectral Range of the resonator with embedded periodic defects. The Free Spectral Range increases as the wavelength drifts away from the band-edge, as well as the peaks' width.

Figure 1B:
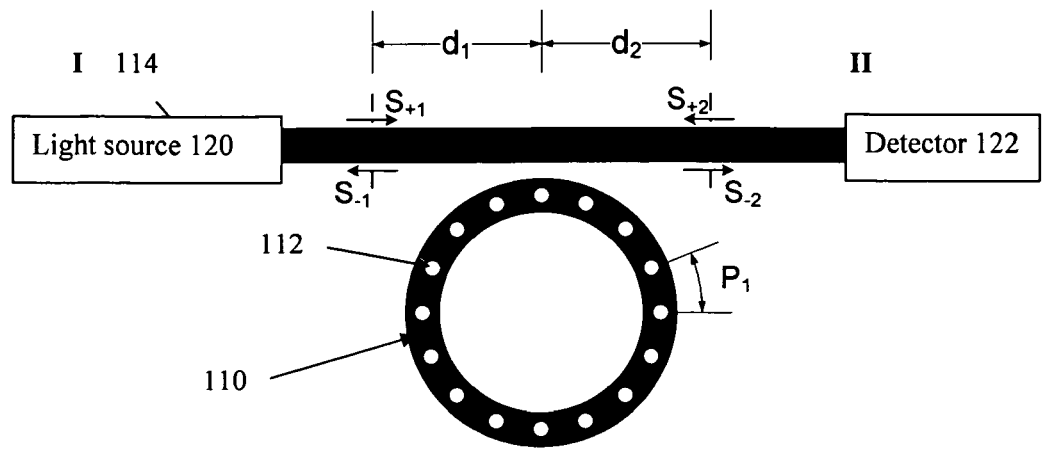
FIG. 1b schematically illustrates an example of the resonator structure according to one embodiment of the present invention.
Figure 1C:
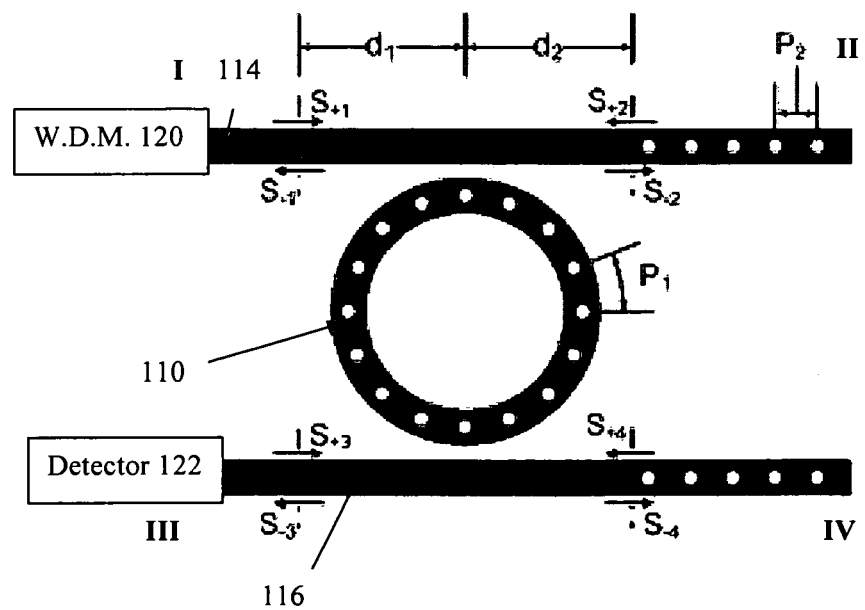
FIG. 1c schematically illustrates another configuration of the resonator structure according to another embodiment of the present invention.

Reference is made to FIGS. 1b-c illustrating the structure of such a resonator with embedded periodic defects, i.e. two highly dispersive micro-ring configurations.

FIG. 1b illustrates a notch filter configuration in which the resonator structure 110 is configured as a micro-ring resonator comprising a series of periodic defects 112 embedded in the resonator 110.

In some embodiments, the resonator 110 is configured as a micro-ring resonator having a diameter of about 100 µm.

The notch filter configuration includes a single coupling waveguide 114 and a micro-ring resonator 110 with embedded periodic defects.

The input signal is fed through port I via a light source assembly 120, and is transferred to the resonator 110. The input signal may include a plurality of signals of different wavelengths transmitted through a wavelength-division multiplexing (WDM). The signal is then outputted through port II to a detector 122. In the present example, the light source assembly 120 and the detector 122 are located outside the resonator 110 appropriately optically coupled thereto. This configuration enables transmission from one port and transmission of an output signal from another.

In some embodiments, to enhance the power performance of the notch filter, at least a portion of the coupling waveguide 114 also comprises periodic defects. The periodic defects should have a different period to those of the micro-ring. These periodic defects may be configured as reflecting structures generally designated to prevent light from being coupled to unwanted ports.

FIG. 1c illustrates an add-drop configuration including two coupling waveguides 114 and 116, and a micro-ring 110 with embedded periodic defects. The input signal is fed through port I, and is transferred to the resonator 110. The signal is then outputted at resonance frequencies through port IV.

As mentioned above, reflecting structures may also be added on the coupling waveguides at ports II and IV to ensure maximization of power transfer between ports I and III at resonance frequencies. This configuration enables high transmission efficiency.

It should be noted that the structure period of the reflectors is different from the period inside the ring. The period inside the ring yields a slow light propagating mode used as described above while the period at the waveguides' ports prevents any propagation of modes, i.e., acts as a reflector.

Different types of periodic defects can be introduced inside the resonator structure. It should be noted that although the different types of periodic defects have different distribution of the dielectric structures, they essentially yield similar dispersion curves. The main difference may occur in propagation losses and fabrication complexity.

Figure 2A:
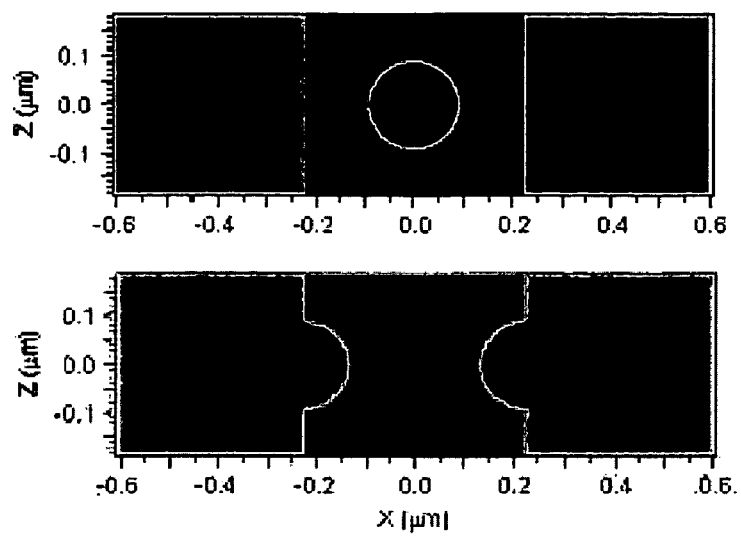
FIG. 2a represents two types of periodic defects embedded into a strip waveguide.
Figure 2B:
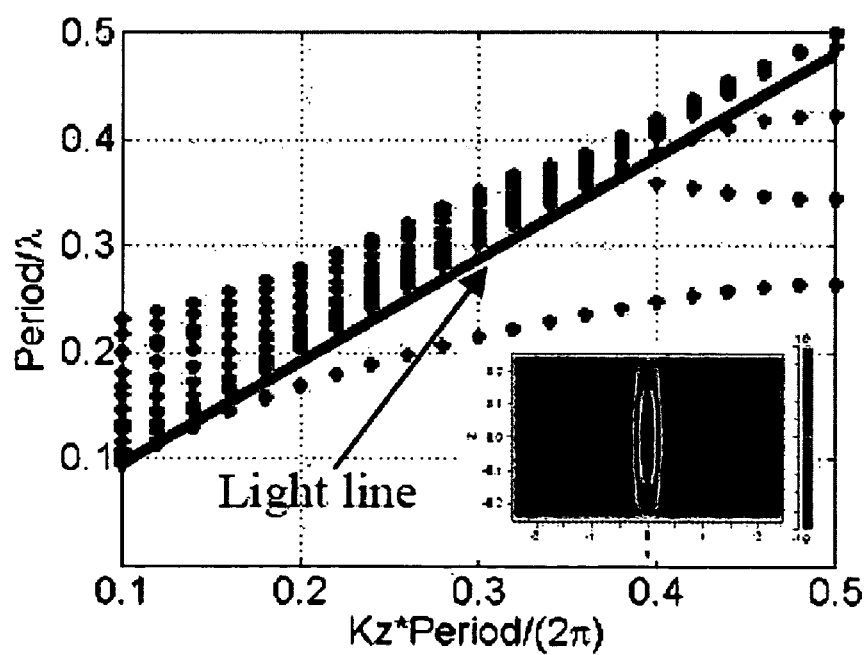

Reference is made to FIG. 2a representing a typical circular hole defect embedded in a waveguide structure as well as a side corrugation defect type. FIG. 2b illustrates the dispersion curve of the resonator of FIG. 2a. The inset depicts the mode profile (Hy field—in plane polarization) of the waveguide's lowest mode. The dispersion curve is calculated using conventional numerical methods. For calculations, the waveguide's core refractive index was 2.798 (equivalent to the effective refractive index of a 240 nm thick Silicon Slab for in-plane polarization), the clad refractive index was 1, the core width was 450 nm and the defect-hole diameter 180 nm. These parameters simulate typical strip silicon waveguides. As can be seen from FIG. 2b, several band-gap regions are formed due to the periodicity and the strong dielectric contrast. More importantly, at the wavelength range, close to the mode band edge, the dispersion curve is flattened and a highly dispersive mode is obtained.

It should be noted that the resonator's radius is large enough, such that the mode's shift due to the bend is small, and the mode can be assumed to be identical to that of a straight waveguide. This assumption is particularly true for silicon waveguides, where the high refractive index of the core leads to strong mode confinement.

The effects of interest occur in the wavelength range where a resonance exists, and also in resonance frequencies within a specific range of propagation constant values, towards the band-edge. Taking into account these two parallel requirements, the period of the structure has to be adjusted such that the band-gap matches the desired operation wavelength (e.g. 1.55 µm for communication applications).

In addition, the resonator perimeter has to make two conditions (i) phase matching, given by:

$$2\pi R \cdot KZ = m \cdot 2\pi \quad (1)$$

where R is the ring's radius, KZ is the mode's propagation constant and m is an integer, and (ii) periodicity. For the Bloch modes to exist, an integer number of periods within the resonator is required, i.e.

$$2\pi R = q \cdot P \quad (2)$$

where P is the period and q is an integer. Equations (1) and (2) impose discrete values of R for given values of KZ and P.

Figure 3:
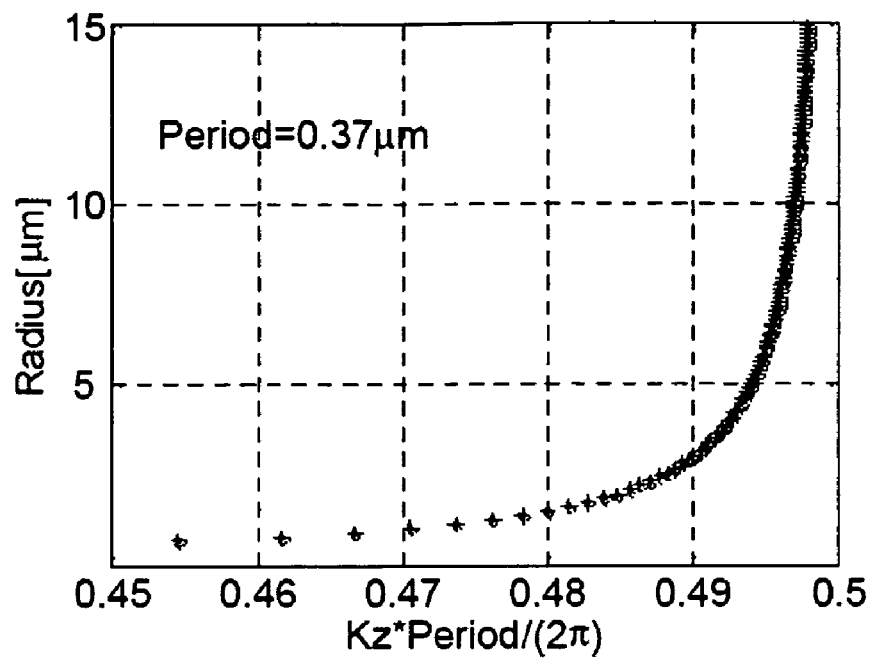
FIG. 3 graphically illustrates resonator radius values satisfying the resonance conditions as a function of propagation constant.

FIG. 3 depicts the minimum possible values of R satisfying resonance conditions as a function of propagation constant (for various values of KZ and a chosen P). It should be noted that according to the results in FIG. 3 a resonator radius of 13 µm (i.e. micro-ring resonator) is sufficient to obtain a group index value of over 50. Moreover, in such a radii values regime, there is an increased amount of KZ values that yield minimum radius values, making the resonator design much simpler. For example, if the radius of the ring is low, any fabrication deviation would impose a significant deviation of the resonance wavelength; while when using larger radii values, the wavelength deviation would be much smaller since there are many solutions that satisfy the minimum radius condition in this region.

Unlike the case of a standard resonator where the resonance wavelengths are almost equally spaced, a rapidly changing free-spectral-range (FSR) is observed when approaching the band-edge wavelength and a band-gap region where no resonance exists. The shrinking FSR results from the increase of the group index inside the resonator. A resonator with embedded periodic defects can produce ultra sharp peaks (e.g. small linewidth) yielding ultra-high sensitivity.

The following is a comparison between two pairs of standards and resonators with embedded periodic defects in an add-drop configuration. The resonators with embedded periodic defects are based on the configuration presented in FIG. 1c. Both resonators have a 1D PhC with a period of 0.37 µm. The first resonator with embedded periodic defects includes 100 periods while the second includes 150 periods. Their radii are 5.89 µm and 8.83 µm respectively. The waveguide-resonator separation is set to 400 µm in both resonators. This pair of resonators with embedded periodic defects was compared to a second pair of resonators with a standard add-drop configuration and parameters identical to those of the resonators with embedded periodic defects (Radius and waveguide-resonator separation). For the comparison, the in-waveguide reflectors of the resonator with embedded periodic defects are located (see FIGS. 1b-c) at a specific distance so that the resulted phase, θ is equal to π/2. The latter ensures that the coupling decay rate multiplier is equal to unity and thus the multiplier does not affect the spectral width of the resonator's response.

Figure 4:
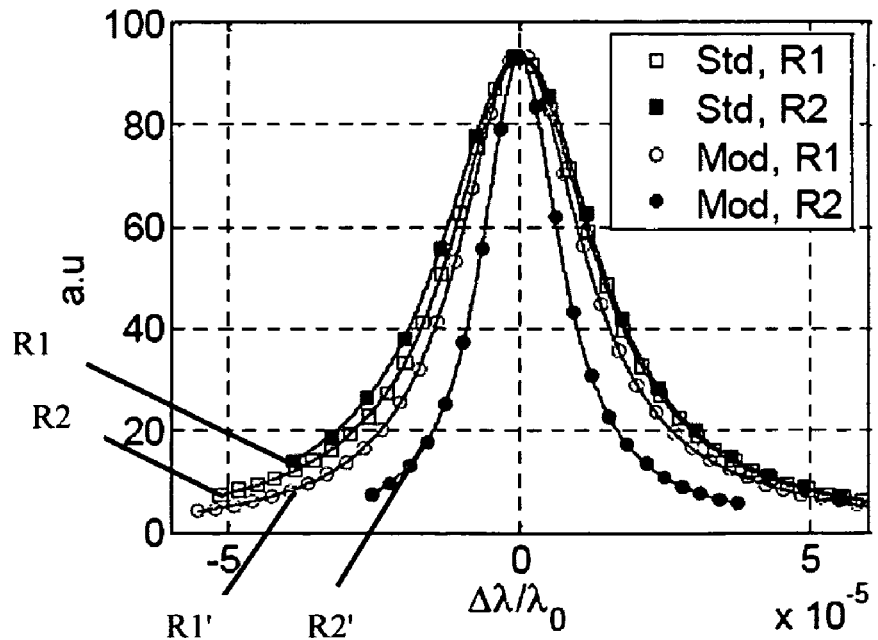
FIG. 4 graphically illustrates a comparison between the frequency response near resonance of standard resonators and resonators with embedded periodic defects.

FIG. 4 presents the resulted transmission peaks. The transmission peaks from the two standard resonators are denoted R1 and R2, while the transmission curves from the two resonators with embedded periodic defects are denoted R1' and R2'. The transmission from both resonators with embedded periodic defects is narrower compared with the transmission obtained by the standard resonator. This narrower transmission implies higher Q-factors for the resonators with embedded periodic defects. An even more interesting outcome of FIG. 4 is found when analyzing the peak width. When increasing the resonator radius, several processes affect the photon decay rate in the resonator: (i) increase in coupling into the waveguide, correspondingly increasing the photon decay rate; (ii) the resonator perimeter is increased, leading to a decrease in the photon decay rate; (iii) stronger dispersion due to closer proximity to the band-edge, further decreasing the decay rate (this effect is true only for the resonator with embedded periodic defects). Thus, when increasing the resonator radius, there is competition between two (standard MRR) or three (MRR with embedded periodic defects) factors that may lead eventually to either an increase or a decrease in spectral linewidth. As illustrated in FIG. 4, for standard MRR, the width is slightly increased with the increase of the MRR radius, while a much more significant decrease in peak width is obtained for the MRR with embedded periodic defects. Therefore, the third factor, i.e., the increase in dispersion of the MRR with embedded periodic defects, is probably the major reason for the increase in Q-factor.

Figure 5:
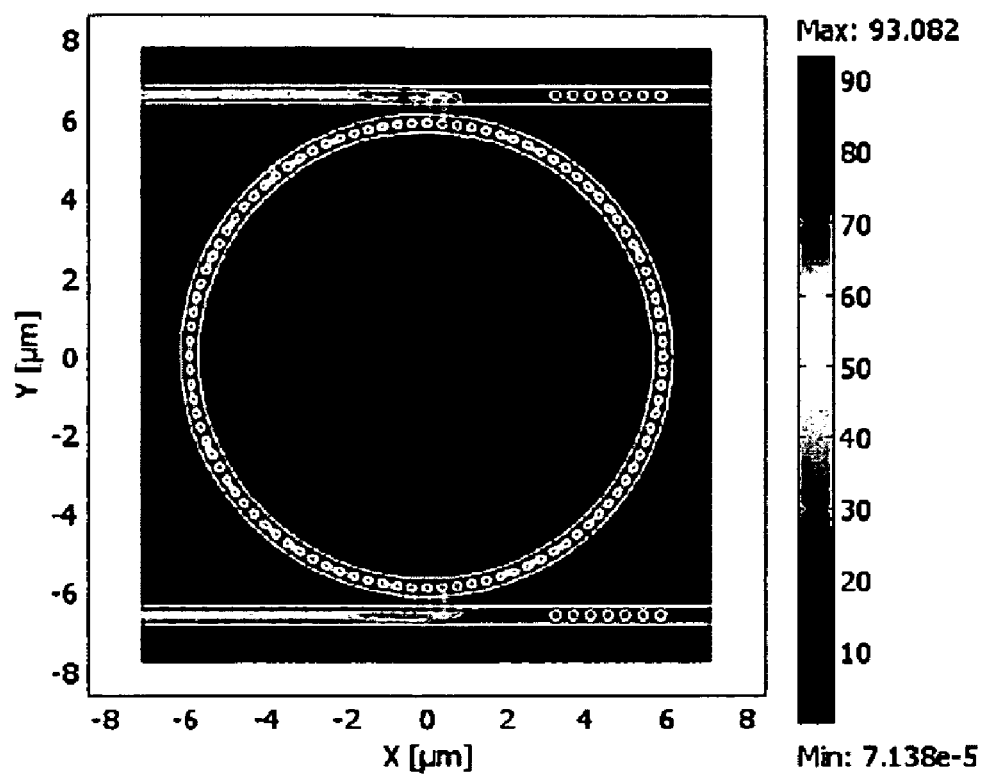
FIG. 5 graphically illustrates the power flow in a resonator structure with embedded periodic defects.

FIG. 5 depicts the power flow in the resonator with embedded periodic defects of FIG. 1c. The power flows into the system from the upper waveguide and is transferred to the lower waveguide through the resonator. The incident optical field is fed into port I. As illustrated in the figure, in the lower waveguide the optical power propagates equally towards the left and the right (port III and port IV).

Therefore, the increase of the resonator's quality factor has been demonstrated by comparing the frequency response of standard and MRRs with embedded periodic defects with similar parameters. It should be noted that it can also be demonstrated by comparing the MRR's with embedded periodic defects peaks as the resonance wavelength gets closer to the band edge (see reference [3] incorporated herein by reference).

Figure 6:
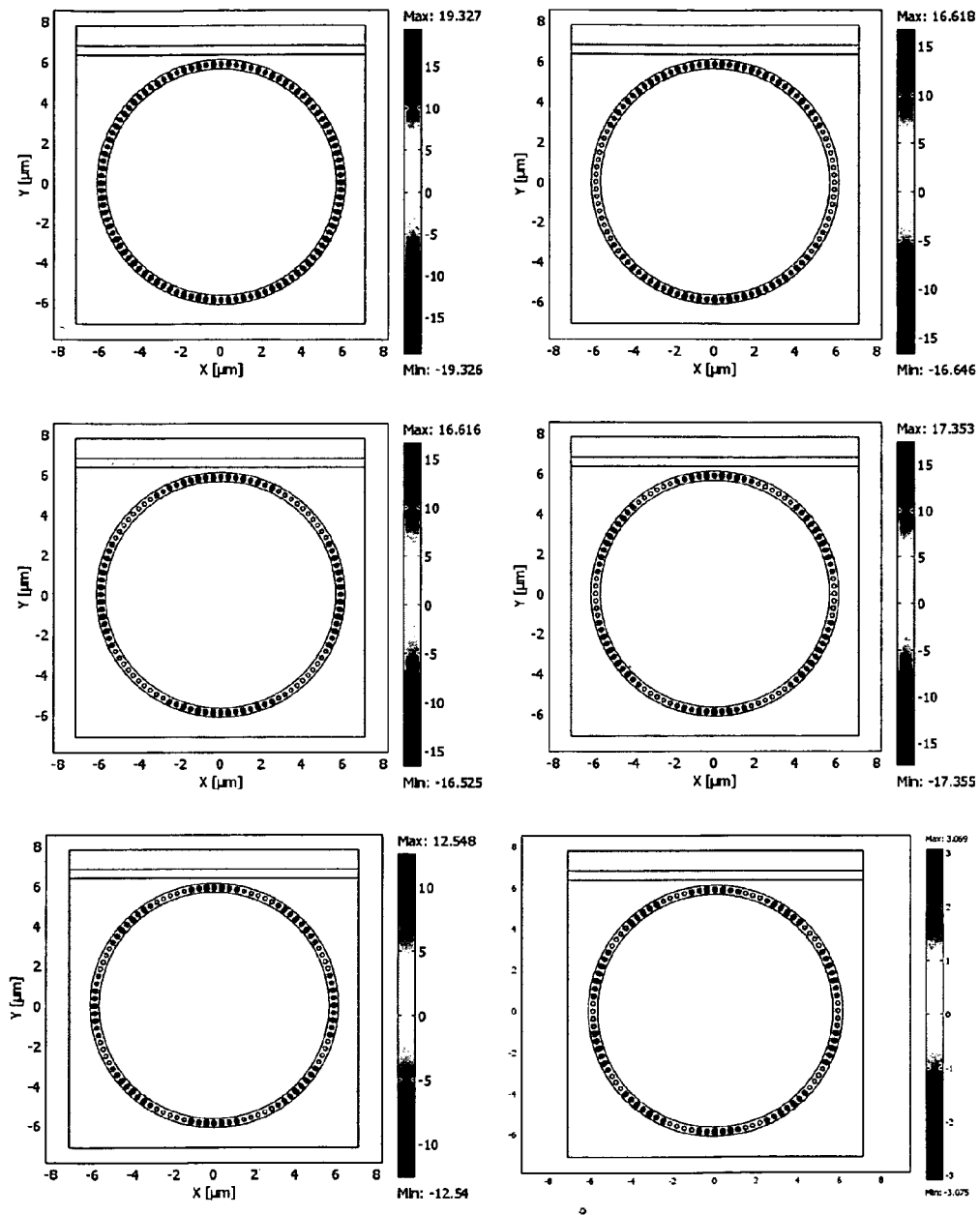
FIG. 6 graphically illustrates the spatial distribution of the electrical field in the resonator with embedded periodic defects of the present invention at the first six resonances of the resonator.

FIG. 6 depicts the spatial distribution of the electric field in the MRR with embedded periodic defects of the present invention at the first six resonances of the resonator ($1^{st}$—closest to the band-edge). Different distributions are observed for the different transmission peaks. Due to the periodic nature of the medium in the resonator, the resonant modes' field distribution is not plain sinusoidal (as in regular resonators). The field distributions have an envelope function that is multiplied with the sinusoidal function. The closest transmission peak to the band-gap obtains a single lobe envelope function. The second peak closest to the band-gap has a two lobe function; the next peak has a three lobe function and so on. In most distributions, high field and low field regions are observed in the ring enabling spatial sensing since a low field region is less sensitive to external materials than a high field region. This special field distribution enables performing spatial sensing in the vicinity of the resonator. Furthermore, the above property enables spectral coding for different materials, i.e., greatly increased sensing.

In some embodiments, the micro-ring resonator with embedded periodic defects of the present invention with a radius larger than 10 µm produces an order of magnitude increase in the Q-factor.

The highly dispersive MRR are useful for a large variety of applications ranging from optical delay lines through various types of communications filters to enhancing nonlinear effects to ultra sensitive sensors. Also due to the circular nature of the MRR with embedded periodic defects it might be useful for Sagnac effect applications, such as optical gyroscopes. The spatial nature of the field modes in the MRR with embedded periodic defects enables micro-scale spatial sensing and performing spectral coding of spatially distributed substances. In addition, the MRR with embedded periodic defects can be used to improve the quality of standard MRR EO modulators enabling either reducing the voltage needed for modulation or reducing the resonator's size.

In some embodiments, the sensor is wavelength selective. The wavelength-selective modulation property of the resonator can be used for building wavelength division multiplexing (WDM) interconnections. The small insertion loss of the resonator makes it possible to cascade multiple resonators along a single waveguide and modulate each WDM channel independently. It should be noted that in this implementation, the resonant wavelength of each ring resonator has to be equal to the wavelength of the corresponding WDM channel.

Figure 7A:
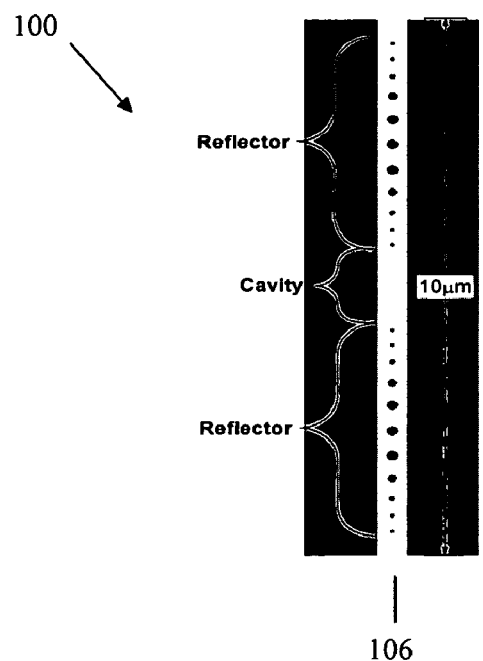
FIG. 7a schematically illustrates a top view of a modulator according to one embodiment of the present invention.

Reference is made to FIG. 7a illustrating a modulator 100 based on a Fabry-Perot configuration with an embedded MOS capacitor. It should be noted that in the figure, the oxide buffer is disregarded for presentation reasons. Within the waveguide 106, two reflectors forming a Fabry-Perot resonator are located within the ridge SOI waveguide 106. The reflectors may be configured as a 1D photonic crystal reflector. The reflectors may be formed by etching holes or other types of structures into the top silicon layer 102 (shown in FIG. 1a).

Figure 7B:
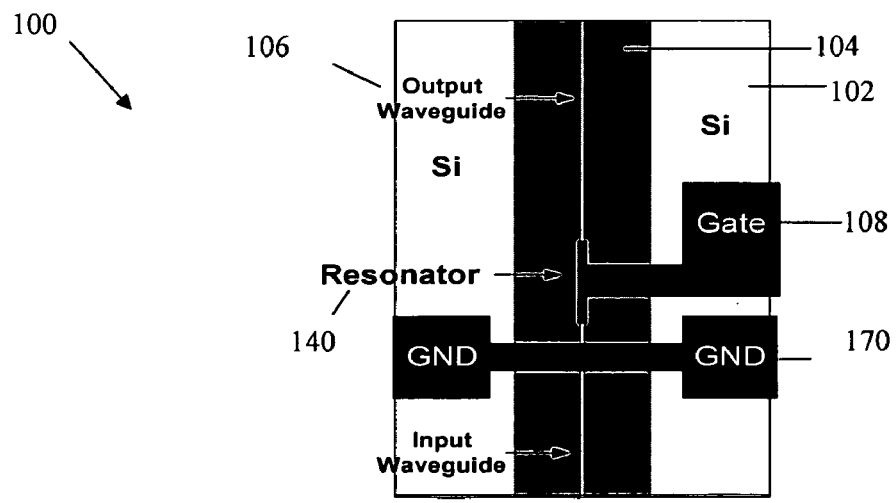

Reference is made to FIG. 7b, illustrating the electrode configuration in the modulator 100 of the present invention. On top of the resonator 140, a gate electrode 108 separated from the silicon layer 102 by an oxide buffer 104 is implemented. This electrode 108 and a ground (GND) electrode 170 placed outside the modulator on the input (or output) waveguide form the MOS capacitor that produces the modulation inside the resonator 140. In order to deposit the oxide buffer 104, the whole resonator 140 was covered with a SiO2 layer 104. The gate electrodes 108 are located above the waveguide part of the modulator 100 in the diagonal direction as illustrated in FIG. 7b, in order to produce a refractive index modulation in the resonator 140.

It should be noted that, since the index modulation induced by carrier modulation is rather weak, the distance between the gate electrode and the waveguide must be as small as possible. On the other hand, the electrode, regardless of its material, creates in-cavity losses (diffraction, insertion etc.) therefore, to prevent quality factor degradation, it is preferable to locate the electrode as far as possible from the waveguide. Generally, a metal gate electrode region adds significant optical losses if its distance to the Si waveguide is too short, since it would overlap significantly with the optical mode field. The present invention solves the above problem by configuring the modulator such that the electrodes yield a relatively strong electrical field in the vicinity of the optical resonator and at the same time have a very small overlap with the optical mode yielding low optical losses and high modulation depth for the modulator. The configuration includes having an electrode structure around the resonator so that the electrode structure still performs its electrical role of inducing changes in carrier density in the top silicon layer. The novel structure has a small spatial overlap with the optical mode leading to small optical losses. Such small losses improve the modulator's quality. For example, for a given modulators' volume of about 0.125 $\mu m^3$ Q-factors larger than 10000 can be obtained. Small operation voltage (inferior to 2V) is therefore needed for the modulation. The electrical field created in the center of the electrode structure is large, yielding strong optical modulation (e.g. superior to 10 dB).

The modulator may be based on MOS capacitor in SOI chips. The resonator of the modulator is not restricted to a specific type of resonator in SOI.

In some embodiments, the modulator's resonator may be configured as a 1D photonic crystal (PhC) cavity resonator, a ring resonator, or a 2D PhC cavity resonator etc.

Figure 8A:
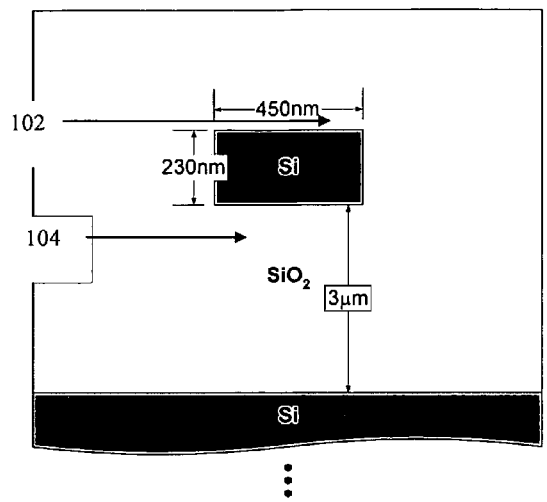
FIGS. 8a-b illustrate the cross-section of the waveguides implemented in the modulator of the present invention with (b) and without (a) a hole in the top silicon layer.
Figure 8B:
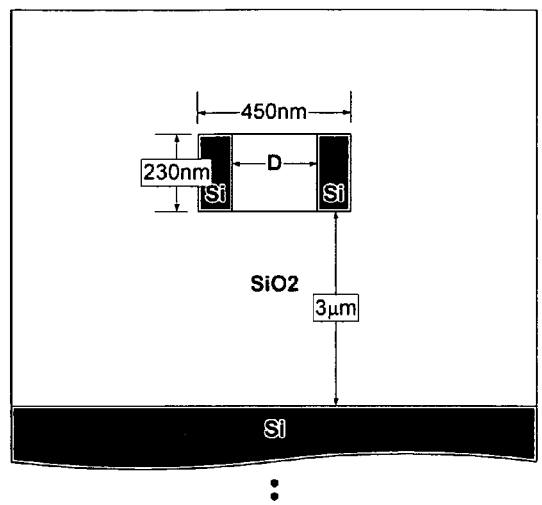

Reference is made to FIGS. 8a-b illustrating two different configurations of the waveguide in the modulator. The cross-section of two waveguides is represented (a) without and (b) with a hole in the top silicon layer 102. The configuration illustrated in the cross-section of FIG. 8a may be implemented inside the modulator and in standard strip waveguides while the configuration illustrated in the cross-section of FIG. 8b may be implemented in the hole areas forming the reflectors.

Figure 9A:
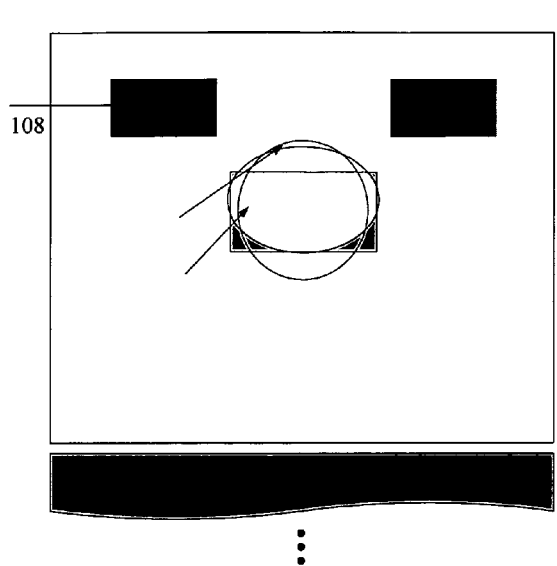
FIGS. 9a-b show the cross-section of the modulator in the area of the cavity that includes the gate electrode (a) the GND electrode (b)

Reference is made to FIG. 9a illustrating a cross-section of the modulator in the area of the cavity (e.g. resonator) comprising the gate electrode 108. The gate electrode 108 can be made of poly silicon or metals to obtain good quality and low cost electrodes, however, if further reduction of the cavity losses is needed, then conductive and transparent electrodes such as ZnO:Al, In2O3, IR-ITO and Carbon-Nanotubes (CNTs) sheets can be utilized. It should be noted that the transparency of the electrode allows light to pass directly from the electrode through to the waveguide, reducing insertion losses. These materials usually have low reflectance and losses and also exhibit low refractive index, and therefore are better than poly silicon having an index of ~3.4.

It should be noted that conventionally, the gate electrode is positioned just above the waveguide inducing an overlap between the electric field generated by the gate electrode and the optical mode propagating inside the waveguide.

As illustrated in FIG. 9a, in this specific example, the gate electrodes 108 are positioned in the diagonal direction above the silicon top layer 102 to yield a relatively strong electrical field in the vicinity of the optical resonator and at the same time have a very small overlap with optical mode yielding low optical losses and high modulation depth for the modulator. The EO modulator may include only one gate electrode placed at an optimized location above the resonator and having optimal shape to prevent the overlap of the optical mode. The electrode structure induces changes in carrier density in the top silicon layer with a small spatial overlap with optical mode leading to small optical losses. The electrical field created in the center of the electrode structure is large, yielding strong optical modulation.

This novel configuration enables using modulators with lower quality factor, and/or using smaller voltage for modulation and/or yielding deeper modulation. It should be noted that higher quality factor signifies that the spectral shape of the transmission function of the modulator is sharper. The sharper the shape is, the smaller the change in refraction index is needed to shift the modulator from transmission mode to blocking mode. Smaller change of refraction index requires lower voltage of operation. On the other hand, if lower voltage of operation is less needed, a modulator having a lower quality factor can be utilized since the losses induced by the electrode(s) would not be too large.

Figure 9B:
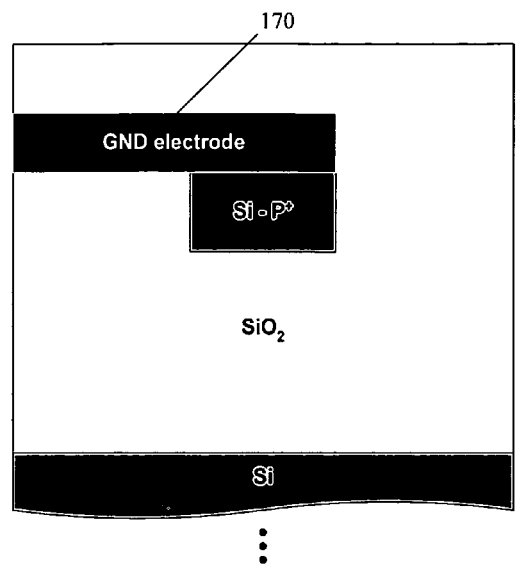

Reference is made to FIG. 9b illustrating the cross-section of the modulator in the area that includes the ground (GND) electrode 170. The GND electrode 170 is connected to the waveguide 106 via the top silicon layer 102 to enable carriers' movement inside the modulator 100. The GND electrode 170 is configured and operable to inject and extract the carriers into and out of the resonator. Since the top silicon layer is a semi-conductor, the potential imposed by the GND electrode is transferred via the top silicon layer. In some embodiments, the GND electrode 170 is located at close proximity to the resonator but not in the resonator itself to provide a spacer between the GND electrode and the field propagating in the waveguide, thereby reducing losses in the optical signal.

Figure 10:
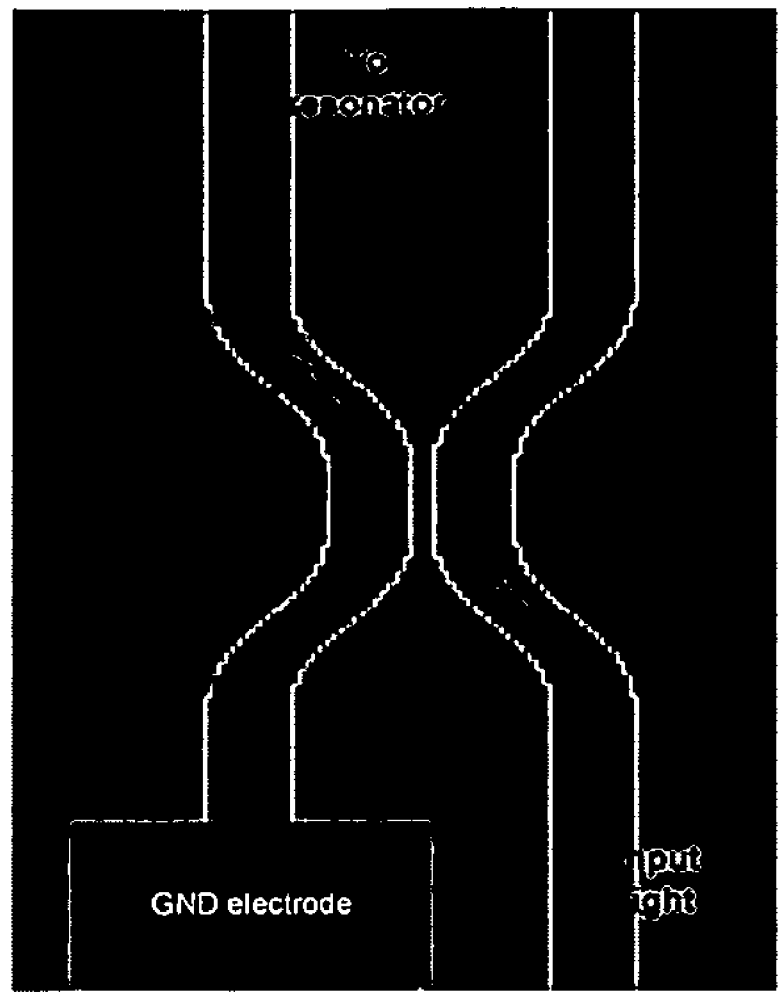
FIG. 10 represents a GND electrode positioning scheme in case of metallic electrode.

In some embodiments, to reduce optical losses induced by the GND electrode, an optical directional coupler may be used before the cavity (e.g. resonator), as illustrated in FIG. 10. Using this configuration, the GND electrode is electrically connected to the modulator, while the optical signal does not pass through the GND electrode. The coupler is configured as a short optical transmission path to transfer the optical signal from one input port to the modulator, when the ground electrode is placed on the second input port. In this way the optical losses are not induced by the ground electrode, which is kept electrically isolated from the modulator.

In some embodiments, FIG. 1a illustrates an add-drop configuration including two coupling waveguides 502 and 504, and a longitudinal modulator 500. The input signal is fed through port I, and is transferred to the modulator 500. The signal is then outputted at resonance frequencies through port IV. When light of the appropriate wavelength is coupled to the modulator 500 by the input waveguide 502, it builds up in intensity over multiple trips in the longitudinal cavity due to constructive interference. It can then be picked up by a detector waveguide 504. Since only some wavelengths resonate in the resonator cavity, it functions as a filter. In this configuration, two coupling curved folded waveguides are accommodated adjacent to the modulator, facilitating light coupling in and out of the modulator. This configuration enables complete electrical isolation of GND electrodes from the modulator as detailed above in which the optical signal does not pass through the GND electrode, preventing optical losses. Moreover, the present invention provides a straight EO modulator optically coupled to at least one input/output waveguide. It should be noted that this configuration enables to provide a compact modulator (about 0.25 $\mu m^3$) having a large Free Spectral Range of more than 400 nm. Two reflectors 506 forming a Fabry-Perot resonator are located within the ridge modulator 500.

Figures 11A, 11B:
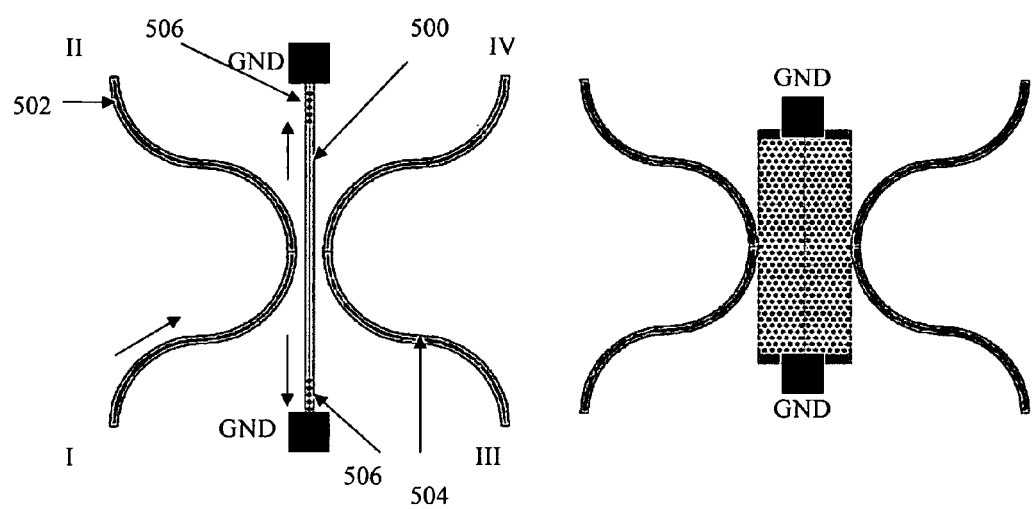
FIG. 11a shows a cross-section of the modulator associated with two coupling curved folded waveguides.
FIG. 11b illustrates the same wherein the modulator is formed in a 2D photonic crystal.

FIG. 11b illustrates another configuration for the modulator in which a 2D photonic crystal is used to form the resonator.

Figures 12A, 12B:
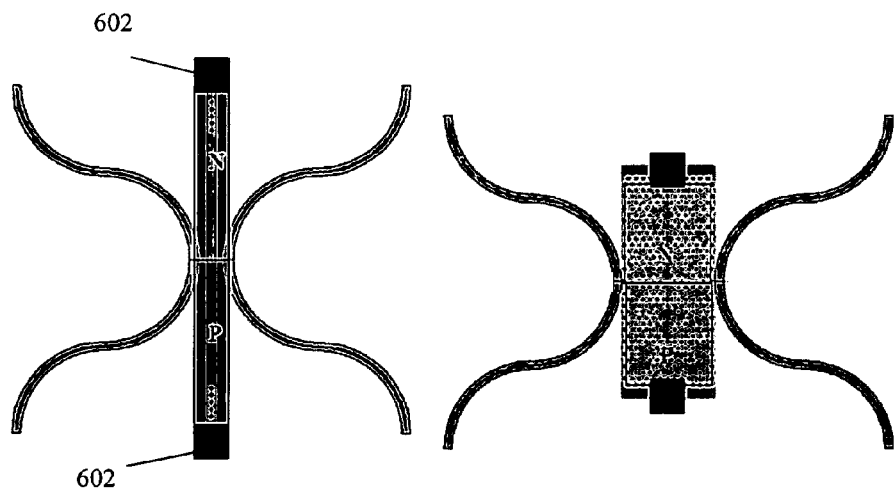
FIG. 12a shows a cross-section of the modulator associated with two coupling curved folded waveguides in which a PN junction is used for the modulation of the refractive index in the resonator.
FIG. 12b illustrates the same as FIG. 12a, wherein the modulator is formed in a 2D photonic crystal.

In some embodiments, a PN junction (instead of MOS capacitor) may be used for the modulation of the refractive index in the resonator, as illustrated in FIG. 12a. By applying a voltage difference between the modulator's contacts 602, the free carriers' concentration in the waveguide can be modulated, modulating the resonator's refractive index. FIG. 12b illustrates a PN junction made in a 2D photonic crystal.

While this invention has been particularly shown and described with references to preferred embodiments thereof, it will be understood by those skilled in the art that various changes in form and details may be made therein without departing from the scope of the invention encompassed by the appended claims.

What is claimed is:

1. An electro-optical modulator for modulating incoming light having a certain wavelength range comprising: a waveguide layer accommodating at least one resonator having a periodic complex refraction index distribution structure defining a periodic defect band-gap and band-edge, a cladding layer, and at least one electrode; said waveguide layer, said cladding layer and said electrode forming a capacitor structure; such that when an external voltage is applied to said capacitor structure the free carrier concentration in the waveguide layer is controlled, enabling a modulation of the resonator's refractive index; wherein said periodic defect band-edge is selected to be within said wavelength range and a period of said periodic refraction index distribution structure is adjusted such that the periodic defect band-gap matches an operation wavelength of said incoming light thereby enabling a slow-light propagation of said incoming light within said waveguide layer.

2. The modulator of claim 1, wherein said resonator is configured as a closed-loop resonator.

3. The modulator of claim 2, wherein said resonator is configured as a micro-ring resonator.

4. The modulator of claim 2, wherein the radius of said resonator is adjusted to satisfy resonance conditions.

5. The modulator of claim 1, wherein said periodic distribution structure is configured as a 1D photonic crystal.

6. The modulator of claim 1, wherein said resonator is optically coupled to at least one input/output waveguide.

7. The modulator of claim 6, wherein at least a portion of said input/output waveguide has a periodic complex refraction index distribution structure.

8. The modulator of claim 7, wherein said portion is located outside the coupling region between the input/output waveguide and the resonator.

9. The modulator of claim 1, wherein the modal dispersion increasing within said resonator enables a reduction in the Free Spectral Range (FSR) of the resonator; said resonator generating ultra sharp peaks yielding ultra-high sensitivity.

10. The modulator of claim 1, wherein said resonator is made in a silicon substrate.

11. The modulator of claim 1, configured and operable as a sensor.

12. The modulator of claim 11, wherein said sensor is wavelength selective.

13. The modulator of claim 11, wherein said resonator generates a spectral response enabling both low and high sensitivity wavelength selection resulting in a wide dynamic range wavelength selection.

14. The modulator of claim 11, wherein said sensor is configured and operable to sense at least one of the followings: laser conditions and temperature conditions affecting the laser operation.

15. The modulator of claim 11, wherein said sensor is configured and operable to identify at least one of the followings: chemical or biological material in the area surrounding the sensor, solid material in the area surrounding the sensor, and spatial distributions of materials in the area surrounding the sensor.

16. The modulator of claim 11, wherein said sensor is configured as an optical gyroscope.

17. The modulator of claim 1, wherein said electrode is located on the cladding layer above the waveguide layer in a diagonal direction respectively to said waveguide layer; such that the electrical field generated by the electrode and the optical mode of the light within the waveguide layer are not overlapping, substantially reducing optical losses in the modulator.

18. The modulator of claim 1, wherein said electrode is configured and operable to enhance the quality factor of the modulator.

19. The modulator of claim 1, comprising a pair of electrodes configured and operable to apply an electrical field to the waveguide layer, wherein said pair of electrodes forms a symmetric structure.

20. The modulator of claim 19, wherein one electrode is a gate electrode and the second one is a ground electrode being located in a spaced-apart relationship with the resonator, providing a spacer between the ground electrode and the optical field propagating in said waveguide layer.

21. The modulator of claim 20, wherein said modulator is optically connected to the output of an optical coupler having one input port in which the light is transmitted, and a second input port in which a ground electrode is located.

22. The modulator of claim 1, wherein said electrode is made of conductor or semiconductor materials.

23. The modulator of claim 1, wherein said electrode is made of transparent material.

24. The modulator of claim 23, wherein said electrode is made of ZnO:Al, In2O3, IR-ITO and Carbon-Nanotubes (CNTs) sheets.

25. The modulator of claim 1, wherein said modulator is based on a Fabry-Perot configuration having two reflecting surfaces.

26. The modulator of claim 25, wherein said reflecting surfaces are configured as 1D photonic crystal reflectors.

27. The modulator of claim 1, comprising at least one other coupling waveguide optically coupled to said waveguide layer, enabling the coupling of said incoming light from said coupling waveguide to said electro-optical modulator.

28. The modulator of claim 27, wherein said electro-optical modulator is configured and operable as an add-drop filter.

29. The modulator of claim 27, wherein said waveguide layer comprises a PN junction configured to modulate the refractive index in the waveguide layer upon application of external voltage.

30. The modulator of claim 27, wherein said waveguide layer comprises a periodic pattern of defects forming at least one of the following: a 1D photonic crystal or a 2D photonic crystal.

31. An optical device to be used with an optical signal having a certain wavelength range; said device comprising at least one resonator having a periodic complex refraction index distribution structure formed by a periodic pattern of defects and defining a periodic defect band-gap and band-edge; wherein a period of the periodic pattern is adjusted such that the band-gap matches the operation wavelength of said optical signal and said periodic defect band-edge is selected to be within said wavelength range, enabling a slow-light propagation of said optical signal within the device.

32. The device of claim 31, wherein said resonator is configured as a closed-loop resonator.

33. The device of claim 32, wherein said resonator is configured as a micro-ring resonator.

34. The device of claim 32, wherein the radius of said resonator is adjusted to satisfy resonance conditions.

35. The device of claim 31, wherein said periodic distribution structure is configured as a 1D photonic crystal.

36. The device of claim 31, wherein said resonator is optically coupled to at least one input/output waveguide.

37. The device of claim 36, wherein at least a portion of said input/output waveguide has a periodic complex refraction index distribution structure.

38. The device of claim 37, wherein said portion is located outside the coupling region between the input/output waveguide and the resonator.

39. The device of claim 31, wherein said resonator enables an increase in modal dispersion within said resonator, inducing a reduction in the Free Spectral Range (FSR) of the resonator; said resonator generating ultra sharp peaks yielding to ultra-high sensitivity.

40. The device of claim 31, wherein said resonator is made in a silicon substrate.

41. The device of claim 31, configured and operable as a sensor.

42. The device of claim 41, wherein said sensor is wavelength selective.

43. The device of claim 41, wherein said resonator generates a spectral response enabling both low and high sensitivity wavelength selection resulting in a wide dynamic range wavelength selection.

44. The device of claim 41, wherein said sensor is configured and operable to sense at least one of the followings: laser conditions, and temperature conditions affecting the laser operation.

45. The device of claim 41, wherein said sensor is configured and operable to identify at least one of the followings: chemical or biological material in the surrounding area of the sensor, solid material in the surrounding area of the sensor, and spatial distributions of materials in the surrounding area of the sensor.

46. The device of claim 41, wherein said sensor is configured as an optical gyroscope.

* * * * *